US009468722B2

(12) United States Patent
Olson

(10) Patent No.: US 9,468,722 B2
(45) Date of Patent: Oct. 18, 2016

(54) MEDICAMENT DELIVERY DEVICE

(71) Applicant: SHL Group AB, Nacka Strand (SE)

(72) Inventor: Stephan Olson, Danderyd (SE)

(73) Assignee: SHL Group AB, Nacka Strand (SE)

( * ) Notice: Subject to any disclaimer, the term of this patent is extended or adjusted under 35 U.S.C. 154(b) by 210 days.

(21) Appl. No.: 14/360,615

(22) PCT Filed: Nov. 21, 2012

(86) PCT No.: PCT/SE2012/051283
§ 371 (c)(1),
(2) Date: May 24, 2014

(87) PCT Pub. No.: WO2013/077800
PCT Pub. Date: May 30, 2013

(65) Prior Publication Data
US 2014/0330214 A1    Nov. 6, 2014

Related U.S. Application Data

(60) Provisional application No. 61/563,659, filed on Nov. 25, 2011.

(30) Foreign Application Priority Data

Nov. 25, 2011  (SE) ...................... 1151121

(51) Int. Cl.
*A61M 3/00*     (2006.01)
*A61M 5/315*    (2006.01)
*A61M 5/20*     (2006.01)
*A61M 5/24*     (2006.01)

(52) U.S. Cl.
CPC ........... *A61M 5/31568* (2013.01); *A61M 5/20* (2013.01); *A61M 5/2033* (2013.01); *A61M 5/24* (2013.01);*A61M 5/3157* (2013.01); *A61M 5/31501* (2013.01); *A61M 5/31586* (2013.01); *A61M 2205/581* (2013.01); *A61M 2205/582* (2013.01); *A61M 2205/583* (2013.01)

(58) Field of Classification Search
CPC ................ A61M 2205/582; A61M 2205/583; A61M 2205/581; A61M 5/3157; A61M 2005/3125; A61M 2005/3126
See application file for complete search history.

(56) References Cited

U.S. PATENT DOCUMENTS

| 5,391,157 A | 2/1995 | Harris et al. | |
|---|---|---|---|
| 2007/0129687 A1* | 6/2007 | Marshall | ................. A61M 5/20 604/207 |
| 2014/0243757 A1* | 8/2014 | Dasbach | ................. A61M 5/20 604/221 |

FOREIGN PATENT DOCUMENTS

| WO | 2004/020028 A1 | 3/2004 |
|---|---|---|
| WO | 2006/079481 A1 | 8/2006 |

(Continued)

OTHER PUBLICATIONS

Sweden Patent Office, Int'l Search Report in PCT/SE2012/051283, Mar. 4, 2013.

(Continued)

*Primary Examiner* — Emily Schmidt
(74) *Attorney, Agent, or Firm* — Piedmont Intellectual Property

(57) ABSTRACT

An injection device includes a housing; a container holder configured for accommodating a medicament container and having a needle attached to one end thereof and a stopper sealingly and slidably arranged inside the medicament container at the other end thereof; a drive unit, including a plunger rod, a plunger driver, and a first energy accumulating member operationally associated with the plunger driver; and an injection indication mechanism, including a tactile signaling element and a drive mechanism for driving the tactile signaling member, the drive mechanism being coupled to the plunger driver.

18 Claims, 14 Drawing Sheets

(56) References Cited

FOREIGN PATENT DOCUMENTS

| WO | 2008/083875 A1 | 7/2008 |
| WO | 2011/039236 A1 | 4/2011 |

OTHER PUBLICATIONS

Sweden Patent Office, Written Opinion in PCT/SE2012/051283, Mar. 4, 2013.

* cited by examiner

MEDICAMENT DELIVERY DEVICE

TECHNICAL AREA

The present invention relates to an injection device having several automatic functions such as automatic penetration, automatic injection and automatic safety means for preventing accidental needle sticks and in particular an injection device capable of handling medicament in fluid form having high viscosity.

BACKGROUND

The present invention relates to injection devices for injecting medicament in fluid form having high viscosity which means that these devices require high forces in order to press the fluid through a needle when injecting the medicament.

Auto-injectors or pen-injectors have been on the market for many years. One of the first auto-injectors was developed for war-times, which was activated by pressing the injector against a body part for activating it. The main concern was to have the medicament injected as fast as possible, without much concern for the patient or for handling safety aspects. During recent years some medicaments have been developed such that these have to be injected by the patients themselves. Therefore, depending on the intended use and type of medicament, injection devices having a varying degree of automatic functions that facilitate the injection of medicaments in a reliable and safe way for patients and even for trained personnel; e.g. physicians, nurses, have also been developed.

Auto-injector devices having an automated injection function often comprise a housing, a spirally wound compression spring acting on a plunger rod which in its turn acts on a stopper inside a medicament container for expelling the medicament through a needle attached to the container. Normally, one end of the spring often abuts an inner end surface of the housing, which means that the housing has to be dimensioned to the force of the spring. When fluids with high viscosity are to be injected using an auto-injector, high forces are required to expel the medicament through a fine needle. Consequently, the spring becomes very large both regarding the diameter of the wound spring and also the diameter of the thread of the wire. The size of the spring means that the device becomes large, and for some applications and customers, such device sizes are not acceptable.

Furthermore, in particular when injection of medicament takes a long tome, for example when a high-viscosity liquid is injected and/or a needle having a small diameter is used, the user of the injection device wants to know whether or not the injection is still proceeding. In other words, the user self-administering a medicament needs to be informed when the injection is completed and it is safe to remove the injector from the injection site.

WO 2004/020028 describes an injection device having a closed scale band. When administering a product, a required dosage is set on the injection device by rotating a rotational button. This transports the scale band in accordance with setting a dosage, such that once the dosage setting rotation is complete, the corresponding dosage unit can be read through a window. Such scale band for dosage indication does however not show the progress of injection.

An injection device having a band type indicator as suggested in WO 2004/020028 is, however, complex to assemble. Moreover, the movement of the band is visible to the user from one direction or viewing angle (or small band of viewing angles) only. Furthermore, slow injections may be difficult to detect by a user.

Another means of information regarding the progress of an injection is by tactile means. Document WO 2008/083875 discloses a medical delivery device comprising a tactile information means capable of providing vibration to the device during e.g. an injection cycle. The vibration is preferably generated by an unbalance member. The tactile information member of the device is rather bulky, especially if it is to be fitted into a rather small device, at the same time as the space usually is limited. Also, vibrations of the whole device may be undesirable in some instances and for some patients, desiring more subtle tactile information.

BRIEF DESCRIPTION OF INVENTION

In order to overcome one or several of the above-mentioned problems, an injection device according to independent claim 1 is provided.

Further aspects, improvements and variations are disclosed in the dependent claims, the figures and the description.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site.

Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The injection device according to the present invention may comprise a housing, which may be one part or several interconnected and attached parts, such as a proximal housing part, a distal housing part and possibly with intermediate housing parts.

One of the housing parts may preferably comprise a container holder arranged within said housing, preferably a proximal housing part if the device is provided with several housing parts. The container holder is configured to accommodate a medicament container having a needle attached to one end thereof and a stopper sealingly and slidably arranged inside said medicament container at the other end.

The device may further comprise a drive unit comprising a plunger rod, arranged to act on the stopper of the medicament container, and a plunger drive means, capable of driving the plunger rod in the proximal direction, thereby moving the stopper. The plunger drive means may be slidably arranged in relation to the plunger rod and may further be rotationally locked to the plunger rod as well as being rotatable in relation to the housing.

The drive unit may further comprise a first energy accumulating member arranged in the interior of the housing of the injection device and adapted to accumulate and store energy. The energy accumulating member may be some sort of spring that may be tensioned in order to provide energy when the plunger drive means is released. Preferably the first energy accumulating member is a spirally wound spring. Said plunger drive means is preferably operationally associated with said first energy accumulating member.

The plunger drive means may preferably be releasable such that due to an output torque from said first energy accumulating member, the plunger drive means is allowed to be rotated and the plunger rod is urged towards the proximal end of the injection device whereby an injection is performed.

According to a main aspect of the invention, the device is arranged with an injection indication mechanism configured for indicating to the user the progress of the injection. The injection indication mechanism may preferably comprise a tactile signalling element and a drive mechanism for driving said tactile signalling member.

The drive mechanism may be coupled to said plunger drive means at the distal end of said plunger drive means, where the injection indication mechanism may be arranged such that the progress of the injection is felt by a user in that said tactile signalling member is protruding out from a distal end surface of the housing. The tactile signalling member thus provides information to the user via e.g. a finger resting on the distal end of the device or another part of the hand of the user, depending on how the user is holding the device during injection.

According to one preferred solution, said tactile signalling element may comprise at least one distally directed protrusion arranged to extend through at least one passage arranged in said end surface of the housing. In this manner, the extension of the protrusion provides positive information regarding the progress of the injection. Preferably the injection device may further be arranged such that said drive mechanism is a rotary drive mechanism rotationally locked to said drive means such that rotation of said rotary drive mechanism during injection drives the tactile signalling member in the distal direction thereby indicating the progress of the injection. In this manner it is possible to utilize the rotating motion of the drive means, which is transferred to the rotary drive mechanism, thereby rotationally driving the tactile signalling member.

In order to transfer the rotational motion to the tactile signalling member, said tactile signalling member may be arranged with thread segments designed to cooperate with corresponding thread segments on said rotary drive mechanism for driving said tactile signalling member. The threaded engagement provides a natural and positive driving force between the components.

When providing the desired, predetermined tactile information, different components of the device may be modified and designed in order to obtain specific characteristics for the signalling member in order to inform the user of the progress of the injection. The pitch of thread segments may be adapted to obtain a predetermined speed of displacement of the tactile signalling member. The length of protrusions may be varied to obtain the predetermined timing or the tactile experience about the progress of the injection. Similarly, an initial position and/or an end position of said tactile signalling member in relation to said distal end surface of the device may be configured to obtain the desired, predetermined characteristics.

For instance the length of the protrusions and/or position of the signalling member in relation to the distal end surface may be chosen such that they protrude somewhat already before the injection sequence, for example signalling that the device is ready for use. The pitch may then be chosen such that the protrusions do not extend so much during the injection sequence, just enough to provide tactile information that the injection is in progress.

On the other hand, the pitch, length and/or position of the signalling member may be chosen such that it protrudes only at the end or last part of the injection sequence, thereby indicating end of injection.

Further to the tactile signalling, the device according to the present invention may also be arranged with an audio signalling member. According to one aspect of the invention, said rotary drive mechanism may further comprise an audio signalling member configured for audibly indicating to the user the progress of the injection, such that the progress of the injection is heard by the user. This feature provides an additional information source that may increase the overall function and response to the device. For instance, the audio signalling member may be operative during the whole injection sequence while the tactile signalling member is only noticeable during the last phase of the injection.

Moreover, the signalling member may also provide some tactile information when said audio signalling member comprises at least one flexible member and at least one impact member. Thereby, during rotation of said rotary drive mechanism, said impact member acts on said flexible member such that it rapidly hits a surface, thereby producing a sound as well as providing vibrational tactile information.

The device may be arranged with further signalling members and in particular said rotary drive mechanism may further comprise a visual signalling member configured for visually indicating to the user the progress of the injection, such that the progress of injection is shown through at least one opening provided at least in a distal end surface of the housing. In this manner the user is also provided with visual information regarding the progress of the injection.

As with the previously mentioned signalling members, a visual signalling member may also comprise at least one indication element for informing the user that the device is ready for a medicament injection, that the medicament injection is in progress, and that the medicament injection has come to an end.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
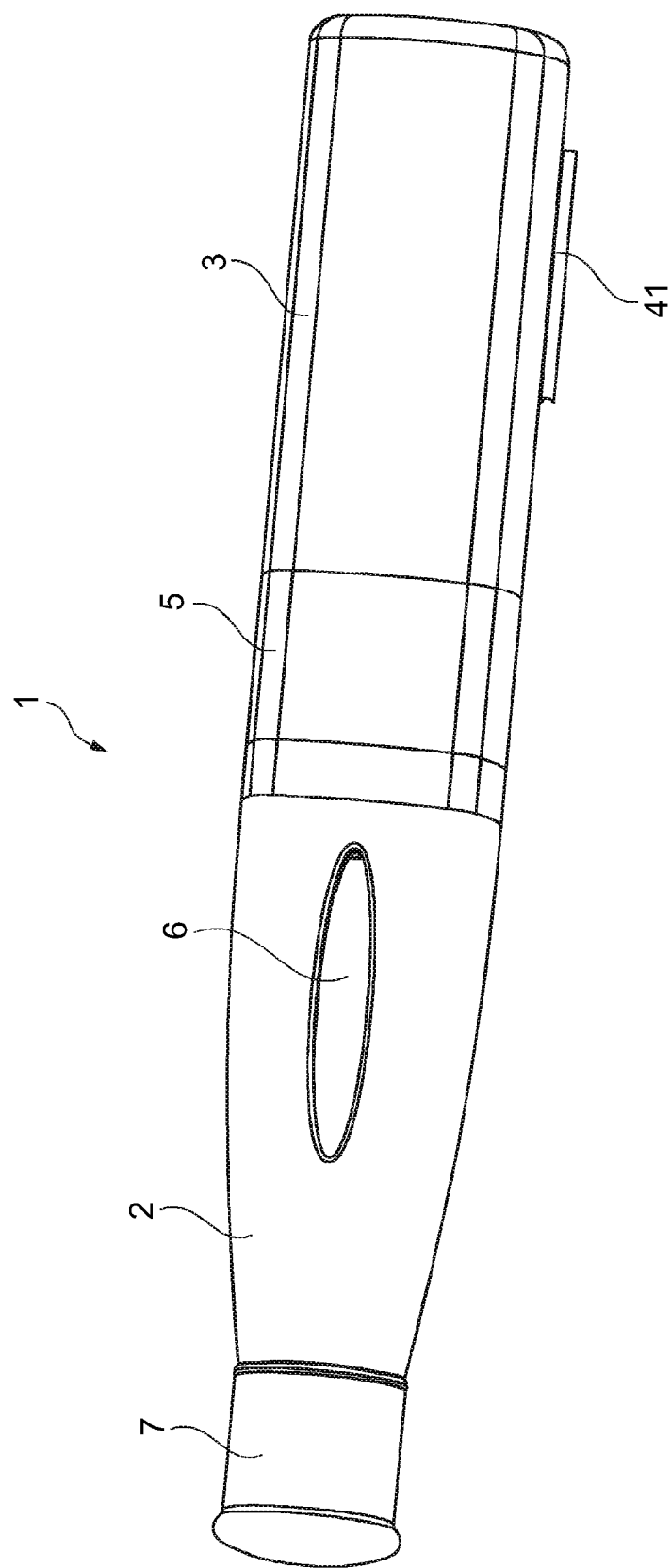
FIG. 1 shows a perspective view of an injection device according to a first preferred embodiment of the invention.

FIG. 1 shows a perspective view of an injection device according to a first preferred embodiment of the present invention. The injection device 1 has a housing that comprises a proximal housing part 2, a distal housing part 3, a proximal intermediate housing part 4 (FIG. 2), and a distal intermediate housing part 5. In the assembled state of the injection device 1, the proximal housing part 2, the distal housing part 3, and the distal intermediate housing part 5 form the outer surface or appearance of the injection device 1.

As shown in FIG. 1, the proximal housing part 2 comprises at least one window 6. In a preferred embodiment, two such windows are provided located at opposite sides of the proximal housing part 2. Such windows allow the user to view the state of the injection, i.e. whether the injection device 1 is still in its initial stage with the medicament not yet being injected, or whether the medicament container is already emptied. Through window 6, the user can see the medicament container accommodated at least in the proximal housing part 2.

Figure 2:
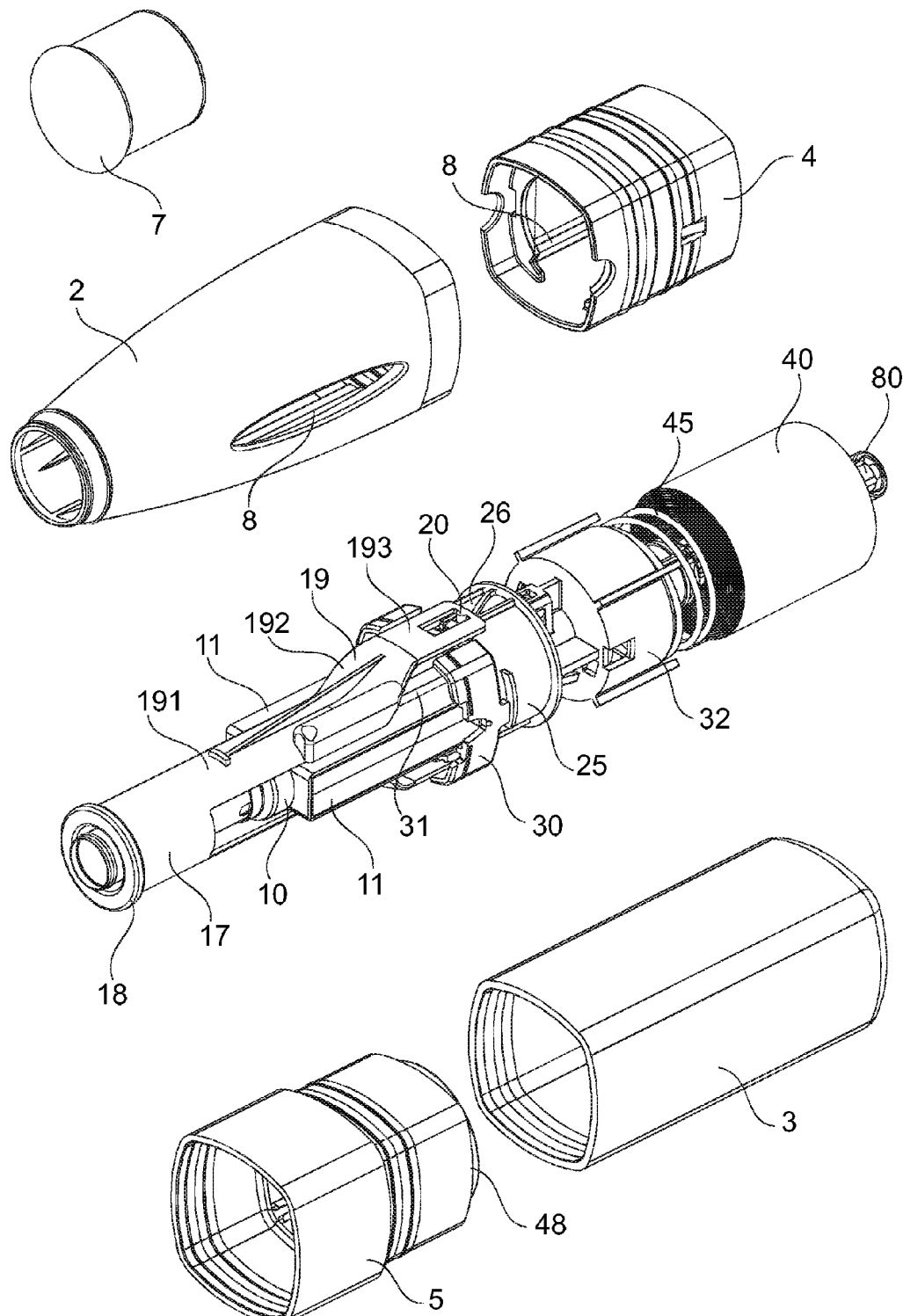
FIG. 2 shows a first exploded view of the injection device according to the first preferred embodiment of FIG. 1.

Furthermore, FIG. 2 shows front cap 7 which closes the proximal opening of the proximal housing part 2 until the injection device 1 is used.

In FIG. 1, the outer end 41 of a spring can also be seen. This will be described in more detail below.

FIG. 2 shows a first exploded view of the injection device 1 according to the first preferred embodiment of the present invention. In this exploded view of FIG. 2, the proximal housing part 2, the distal intermediate housing part 5 and the distal housing part 3, as well as the front cap 7 are shown "removed" from the injection device 1. Furthermore, FIG. 2 shows a proximal intermediate housing part 4. Proximal intermediate housing part 4 forms part of the housing of the injection device 1 but is in fact located in the interior (as clearly shown in the cross-sectional view of FIG. 7) in order to connect the proximal housing part 2 and the distal intermediate housing part 5 with each other. To this end, the outer surface of the proximal intermediate housing part 4 and the inner surfaces of the proximal housing part 2 and the distal intermediate housing part 5, respectively, are provided with corresponding engagement structures such as circumferential groove-rib-structures, a shown in FIG. 2. Thus, the proximal housing part 2 and the distal intermediate housing part 5 can easily be snapped onto the proximal intermediate housing part 4 so that the proximal housing part 2 and the distal intermediate housing part 5 do not fall off of each other. However, the connection between these parts may be releasable so that a medicament container can be inserted into or removed from the proximal part of the injection device 1.

As further shown in FIG. 2, the injection device according to the first embodiment of the invention comprises a medicament container holder 10. In the fully assembled state of the injection device 1, the medicament container holder 10 is at least with its proximal part located within the proximal housing part 2. This will be described in more detail below with reference to FIG. 7. In the preferred embodiment shown in FIG. 2, the medicament container holder 10 comprises a first and a second container holder guide 11. Preferably, the container holder guides 11 are arranged at opposite sides of container holder 10, and extend in longitudinal direction thereof. The container holder guides 11 are received in corresponding groove structures provided at the inner surface of the proximal housing part 2 so that the medicament container holder 10 is axially movable in relation to the housing but is locked from being rotated relative to the housing, in particular relative to proximal housing part 2.

FIG. 2 also shows needle shield sleeve 17 having at its proximal end a needle shield sleeve extension 18. At its distal end, needle shield sleeve 17 comprises two tongue extensions 19 which are arranged on opposite sites, relative to the longitudinal center axis of the injection device 1. The proximal part of needle shield sleeve 17 is of generally cylindrical form. The most proximal part is a fully closed cylinder from which the two tongue extensions 19 project and extend towards the distal end of the injection device 1. In the preferred embodiment shown in the drawings, the tongue extensions 19 basically comprise three areas. The first, most proximal area 191 is formed by two cylinder segments having the same radius/diameter as the closed cylindrical most proximal part of needle shield sleeve 17. The distal parts or areas 193 of tongue extensions 19 are spaced from each other at a greater distance than the diameter of the cylindrical part. In between of these two areas, an intermediate area 192 is provided that forms a transition between the smaller diameter of the cylindrical area 191 and the greater distance at the distal end 193 of the tongue extensions 19. In general terms, the needle shield sleeve 17 has a widened configuration in that it widens from the proximal end towards the distal end thereof.

FIG. 2 further shows proximal housing spring retainer 30 which is generally ring-shaped or substantially ring-shaped, and coaxially arranged with the proximal housing part 2. The proximal housing spring retainer 30 surrounds a distal area of medicament container holder 10, i.e. is located as shown in FIG. 2, radially between a distal area of medicament container holder 10 and the distal areas 193 of tongue extensions 19. As shown in more detail in FIG. 4, the proximal housing spring retainer 30 comprises two pins 31 that carry springs (not shown In FIG. 2) to push the needle sleeve 17 towards the proximal end of the injection device 1 when the injection device 1 is removed from the injection site after medicament delivery has been performed in order to cover the needle 13.

FIG. 2 also shows container driver locking means 25 being a generally ring-shaped element. Container driver locking means 25 is rotatable in relation to the housing and in engagement with the needle shield sleeve 17. This engagement is described in more detail below with reference to FIGS. 3 and 4.

Distal from container driver locking means 25, container driver 32 is located. Container driver 32 is arranged for being connectable to the container holder 10, which will be described in further detail below.

Furthermore, FIG. 2 shows a first energy accumulating member, i.e. first spring 40 which is used to perform an injection, and a second energy accumulating member, for example second spring 45 which is used to axially move the medicament container holder 10 in order to perform a needle penetration prior to injection of the medicament.

Finally, FIG. 2 shows indicator 80 for indicating end of dose.

Further parts shown in FIG. 2 not yet discussed will be discussed in detail below.

Figure 3:
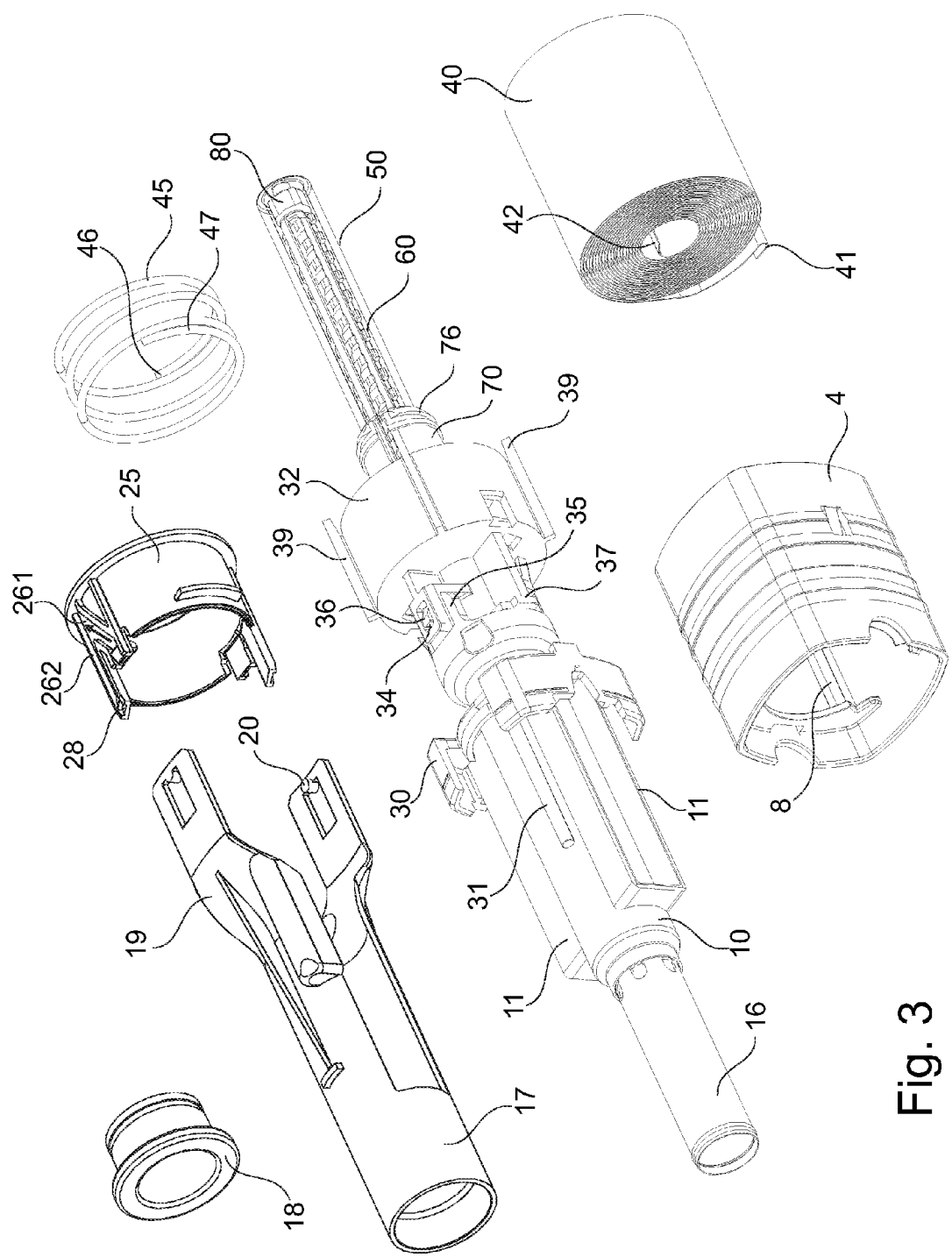
FIG. 3 shows a further exploded view of the injection device according to the first preferred embodiment of the invention.

FIG. 3 shows a further exploded view of the injection device 1 according to the preferred embodiment of the present invention.

In FIG. 3, the needle shield sleeve 17, the needle shield sleeve extension 18, and the container driver locking means 25 are shown "removed" from the injection device assembly. Furthermore, the proximal intermediate housing part 4 and the first spring 40 are shown as individual components in more detail.

In FIG. 3, one of two opposing groove structures 26 of the container driver locking means 25 is shown in more detail. Each groove structure 26 has two segments, namely an inclined groove 261 and a longitudinal groove 262. In the initial position of injection device 1, radial protrusions 20 formed at the inner surface of the distal areas 193 of the tongue extension 19 are located in the inclined groove 261 of the groove structures 26. When the injection device 1 is placed on an injection site, for example the skin of a user, the needle shield sleeve 17 is thereby pushed or moved towards the distal end of the injection device 1. Such displacement of the needle shield sleeve 17 causes the protrusions 20 to move in the inclined grooves 261 towards the distal end of the container driver locking means 25 (which is shown by an arrow and drawn in the inclined groove 261 in FIG. 3). Since the container driver locking means 25 is rotatable in relation to the housing but longitudinally fixed (in that it abuts against the container driver 32), and the needle shield sleeve is rotationally locked, longitudinal displacement of the needle shield sleeve 17 towards the distal end of the injection device 1 results in a rotational movement of the container driver locking means 25, allowing the protrusions 20 to slide towards the distal ends of inclined grooves 261.

As long as the injection device is pressed on the injection site, i.e. as long as the needle shield sleeve 17 is held in its distal position, the protrusions 20 stay at the distal end of the groove structures 26. However, when the user removes the injection device 1 from the injection site, for example after medicament delivery, the needle shield sleeve 17 is urged towards the proximal end of the injection device 1, as described above. During this movement, the projections 20 slide along longitudinal grooves 262 and are locked at the proximal ends of the longitudinal grooves 262 by respective locking structures 28. This prevents that the needle shield sleeve 17 can again be moved towards the distal end of the injection device 1.

FIG. 3 further shows in more detail the medicament container holder 10 with its two container holder guides 11. Furthermore, one of the two pins 31 of the proximal housing spring retainer 30 extending parallel to the longitudinal axis towards the proximal end of the injection device is shown with its full length.

FIG. 3 also shows rigid needle shield remover 16. The rigid needle shield remover 16 comprises at its proximal end an engagement structure, such as a circumferential rib at its outer surface, which is in engagement with a corresponding engagement structure at the inner surface of the front cap 7, for example a corresponding groove (shown in FIG. 7). Due to such engagement, upon removal of the front cap 7, the rigid needle shield remover 16 is withdrawn from the medicament container 12. Furthermore, upon removal of the rigid needle shield remover 16, the rigid needle shield comprising a soft part 14 and a rigid part 15 (see FIG. 5) are also removed from the medicament container 12 due to respective engagement structures engaging the two parts of the rigid needle shield and the rigid needle shield remover 16 with each other.

FIG. 3 also shows in more detail the container driver 32. The container driver 32 comprises at least one rotational locking rib 39. In the preferred embodiment, four rotational locking ribs 39 are provided, three of which are shown in FIG. 3. In the assembled state of the injection device 1, the rotational locking ribs 39 are located or received in corresponding locking grooves 8 arranged on the inner surface of the proximal intermediate housing part 4. The locking ribs as well as the corresponding grooves extend in longitudinal direction. Such structure prevents the container driver 32 from being rotated, i.e. the container driver 32 is movable in longitudinal direction relative to the housing but rotationally locked.

At its proximal side, the container driver 32 comprises at least one container driver arm 33. In the preferred embodiment shown in the drawings, two container driver arms 33 are arranged (see FIG. 4). The container driver arms 33 each comprise an engagement opening 34 being configured for engagement with corresponding engagement protrusions 36 projecting from container holder tongue extensions 35 provided at the distal end of the container holder 10. Thus, the medicament container holder 10 is connected with the container driver 32, and longitudinal displacement of the container driver 32 towards the proximal end of the injection device 1 (by second spring 45) results in a movement of the medicament holder 10 towards the proximal end of the injection device 1 whereby a needle penetration is performed.

Figure 6:
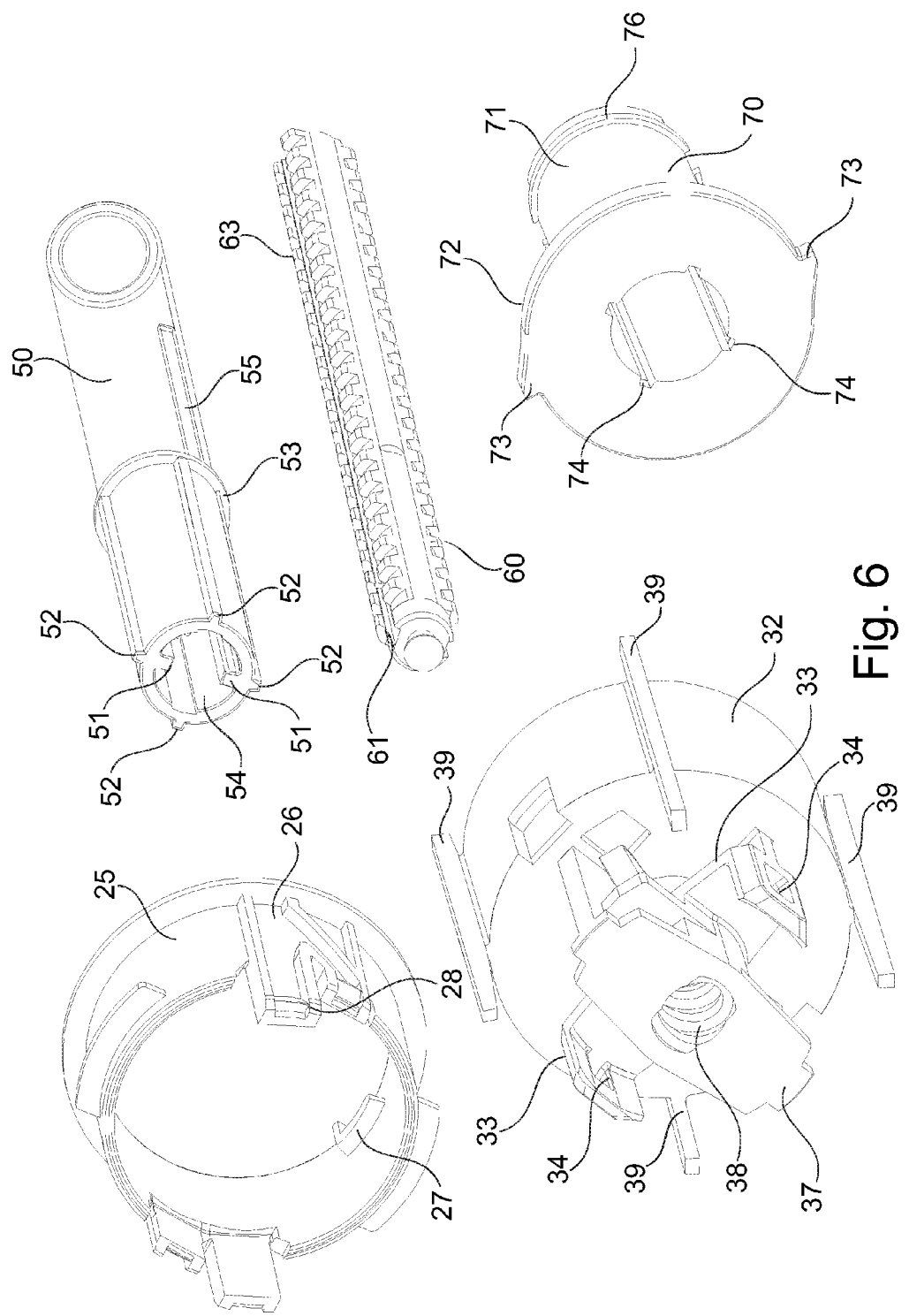
FIG. 6 shows further components of the injection device according to the preferred embodiment.

As can also be seen in FIG. 3, the container driver 32 comprises at least one ledge 37. In the preferred embodiment, two ledges 37 are provided (as can be seen in more detail in FIG. 4). With these ledges 37, the container driver 32 initially abuts against stop ribs 27 located at the inner surface of the container driver locking means 25 (the stop ribs 27 are shown in FIG. 6). Thus, in the initial position of the injection device, i.e., prior to its use, the container driver 32 and thus the medicament container holder 10 are prevented from being moved proximally because such movement is blocked by the container driver locking means 25 due to the abutment of the ledges 37 against the stop ribs 27. Only upon rotational movement of the container driver locking means 25 (caused by distal displacement of the needle shield sleeve 17), the stop ribs 27 are moved out of abutment with the ledges 37. Thus, the container driver is no longer axially locked/blocked by container driver locking means 25.

FIG. 3 also shows plunger driver 50, plunger rod 60, and plunger drive locking means 70. These components are described in more detail below.

Finally, as shown in FIG. 3, first spring 40 comprises an outer end 41 which connects the first spring 40 to the housing, i.e. to the distal housing part 3, and an inner end 42 which connects the first spring 40 to the plunger driver 50. The outer end 41 may, for example, extend through a longitudinal slit in the distal housing part so that it may be engaged with the wall in the form of a hook. The first end 41 can then be seen at the outside, as shown in FIG. 1. Alternatively, the first end of spring 40 is engaged to a mating engagement structure provided at the inner surface of distal housing part 3.

Figure 4:
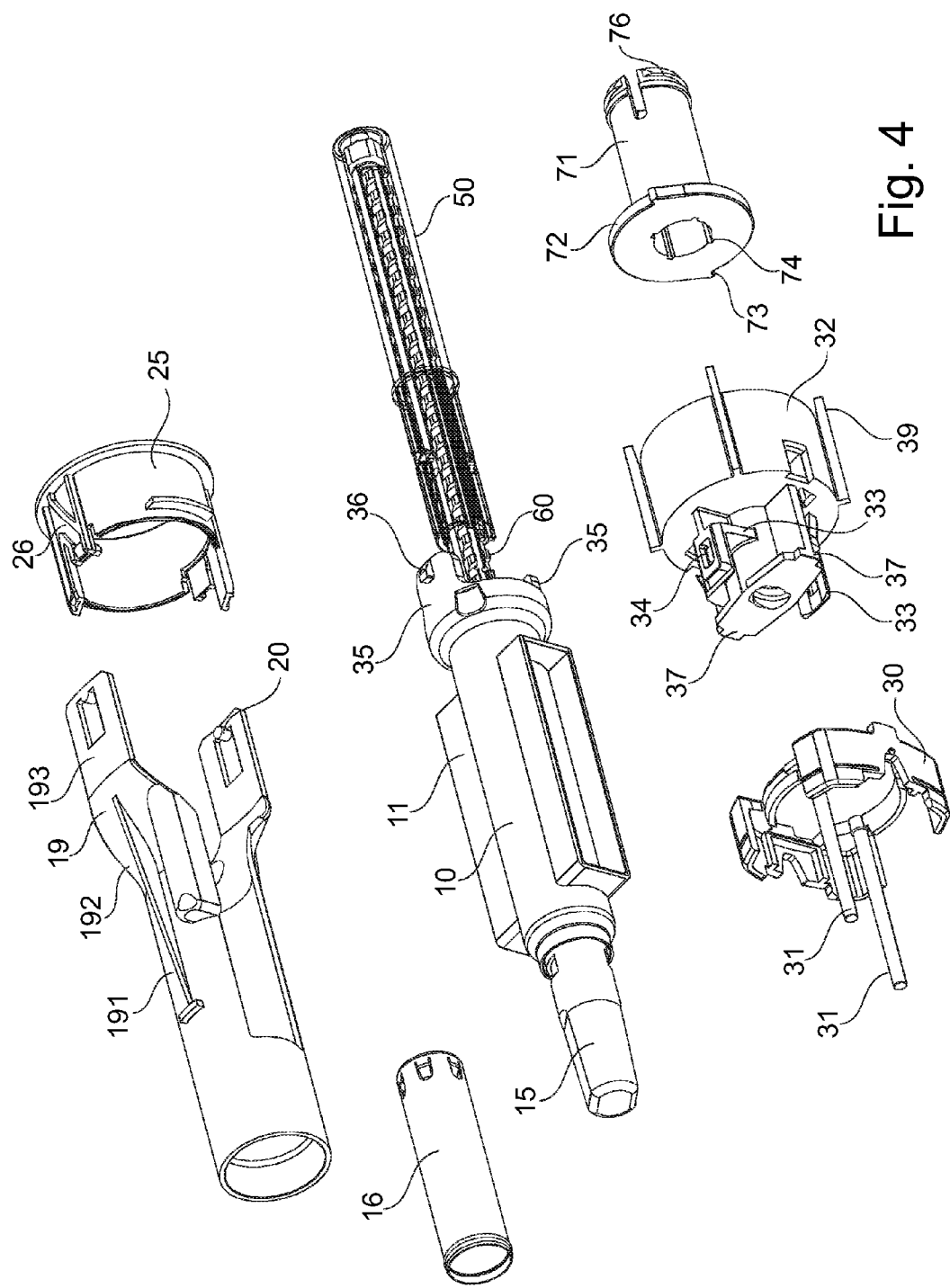
FIG. 4 shows a further exploded view of the injection device according to the first preferred embodiment of the invention.

In the exploded view of FIG. 4, the injection device 1 of the preferred embodiment of the invention is further disassembled. In this drawing, the proximal housing spring retainer 30, the container driver 32, and the plunger drive locking means 70 are shown "removed" from the assembly. In FIG. 4, the distal end of the medicament container holder 10 is shown uncovered by the container driver 32. Thus, the two container holder tongue extensions 35 each having an engagement protrusion 36 can easily be seen.

Furthermore, the two opposing arms 33 of the container driver 32 are shown. In the preferred embodiment, each arm comprises two portions, a first portion extending radially, and a second portion extending in longitudinal direction towards the proximal end of the injection device. Although in the preferred embodiment only two container driver arms 33 and only two corresponding container holder tongue extensions 35 are shown, the invention encompasses other configurations, such as just a single arm-protrusion-pair, or a larger number of arm-protrusion-pairs, such as three or four, for example. Similarly, the container driver 32 may have just a single rotational locking rib 39 but the invention also encompasses container drivers having two, three, five, or six, or even more rotational locking ribs. Furthermore, although the container driver 32 shown in FIG. 4 comprises two ledges 37 for abutment with the container driver locking means 25 only, other configurations having just one or three, four, or more ledges are also encompassed by the invention.

FIG. 4 further shows plunger drive locking means 70. Plunger drive locking means 70 is of generally cylindrical configuration (distal part 71) and comprises at its proximal end radial flange 72. The proximal flange 72 of the plunger drive locking means 70 comprises at least one rotational lock element 73 projecting essentially radially. In the embodiment shown in the Figs, two such lock elements 73 are provided. With these rotational lock elements 73, the plunger drive locking means 70 is initially rotationally locked to the container driver 32. In order to provide such rotational locking, the container driver 32 comprises corresponding longitudinal ribs 75 at the inner surface of its distal part (shown in FIG. 7). The rotational lock elements 73 initially abut against these ribs 75. The axial length of these locking ribs 75 of the container driver 32 is adapted to the length the container driver 32 and the medical container holders 10 are displaced/displaceable to perform a needle penetration. In more detail, the axial length of the locking ribs 75 is such that upon full displacement of the medicament container holder towards the injection site, the rotational lock elements 73 are finally freed from engagement with the locking ribs 75. This means that at this stage the plunger drive locking means 70 is no longer rotationally locked by the container driver 32. In other words, when performing needle penetration, the container holder 32 is moved longitudinally relative to the plunger drive locking means 70. The plunger drive locking means 70 is axially locked. Such axial lock is provided by a locking structure 76 at the distal end of the plunger drive locking means 70 which is in engagement with a corresponding structure at a distal end of the distal intermediate housing part 5 (see FIG. 7).

Figure 5:
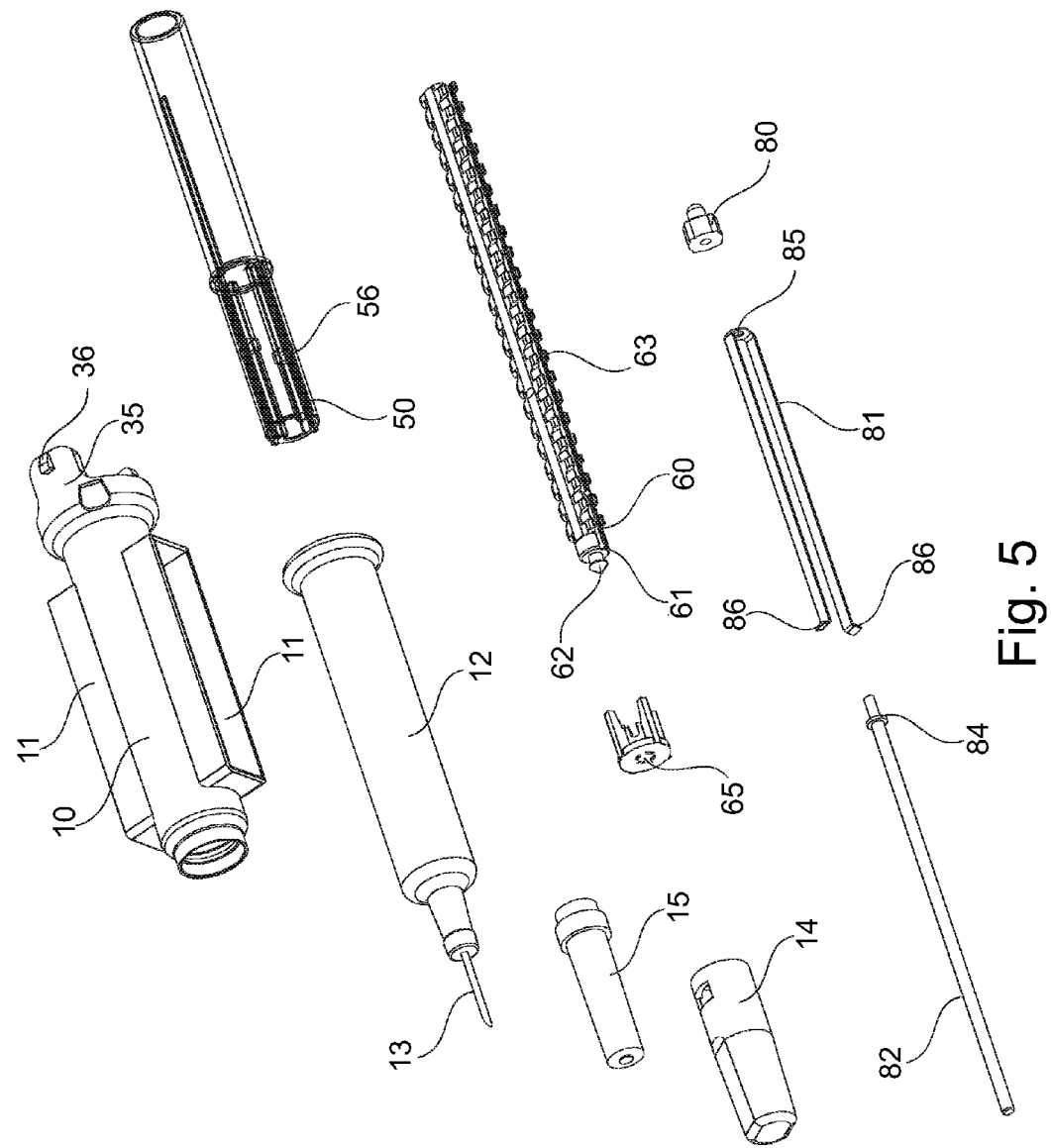
FIG. 5 shows further components of the injection device according to the preferred embodiment.

FIG. 5 shows further components of the injection device 1 according to the preferred embodiment.

As mentioned above, needle 13 of medicament container 12 is covered by a rigid needle shield consisting of a soft part 14 and a rigid part 15.

FIG. 5 further shows plunger driver 50 which is rotationally locked to the plunger drive locking means 70 but slidable in axial direction in relation to plunger drive locking means 70. This will be described in more detail in the context of FIG. 6.

Plunger rod 60 shown in FIG. 5 comprises a threaded structure 63 as well as at least one longitudinal groove 61. At the proximal end, plunger rod 60 comprises a plunger rod tip 62 onto which a spinner element 65 is snap fit. Spinner element 65 acts on the stopper in the medicament container 12.

Finally, FIG. 5 shows an indicator assembly for indicating end of dose, comprising am indicator 80, and a U-bracket 81 arranged between the plunger rod 60 and the plunger driver 50. The U-bracket 81 is connected to the plunger drive locking means 70 such that when the plunger rod 60 is proximally advanced and not in contact with the U-bracket, the U-bracket, the indicator 80 and the indicator rod 82 are forced distally. FIG. 5 also shows indicator rod 82, being also part of the indicator assembly. A spiral spring (not shown in FIG. 5) is coaxially arranged on the indicator rod 82, wherein the spiral spring is arranged within the plunger rod 60. Thus, the indicator rod 82 with the spring is received within a central axial through hole in the plunger rod 60, whereas U-bracket 81 lay with its two legs on the two opposing longitudinal grooves 90 degrees to the two opposing longitudinal grooves 61 of the plunger rod 60.

FIG. 6 shows plunger driver 50. Plunger driver 50 comprises, in the shown embodiment, two internal longitudinal ribs 51. These longitudinal ribs 51 interact with longitudinal grooves 61 on the outer surface of a plunger rod 60. Thus, the plunger rod 60 is rotationally locked to plunger driver 50 but may axially slide along these ribs 51.

Plunger driver 50 further comprises a longitudinal slit 55 though its wall. With this longitudinal slit 55, the plunger driver 50 is connected to the inner end of the first spring 40. Thus, a force applied to the plunger driver 50 by the first spring 40 is transmitted to the plunger rod 60 due to the engagement of internal longitudinal ribs 51 into longitudinal grooves 61.

On the other hand, the plunger driver 50 comprises at least one external longitudinal rib 52. In the embodiment shown, four such ribs are provided spaced at 90° to each other. The external longitudinal ribs 52 are slidably received in longitudinal grooves 74 of the plunger drive locking means 70. Thus, as long as the plunger drive locking means 70 is prevented from being rotated due to the locking engagement with the container driver 32, the plunger driver 50 and the plunger rod 60 are prevented from being rotated although the force of the first spring 40 acts on the plunger driver 50. However, once the plunger drive locking means 70 is free to rotate, the plunger driver 50 and the plunger rod 60 also start to rotate, caused by the first spring 40. In the initial stage of the injection device 1, i.e. prior to its use, a proximal part of the plunger rod 60 is received in the central opening of the container driver 32. As shown in FIG. 6, the central opening of container driver 32 comprises a threaded structure 38 that engages with the threads 63 of the plunger rod 60. Thus, the threaded proximal section of the plunger rod 60 is screw threaded in the interior of the container driver 32. Due to this threaded engagement, rotation of the plunger rod upon use of the injection device results in an axial displacement of the plunger rod towards the proximal end of the injection device. In other words, the plunger rod 60 is rotated by the thread engagement in the direction of the medicament container 12, and causes the stopper (not shown) in the medicament container holder 12 and in abutment with spinner 65 to move towards the proximal end of the medicament container holder in order to expel medicament. The torque force of spring 40 will continue to drive the plunger rod towards the proximal end of the injection device 1 pressing the stopper to expel medicament through the needle 13. The container driver 32 slides over along the plunger rod 60 as the plunger rod continues to move towards the proximal end of the device. The injection is completed when the stopper is at the proximal end of the medicament container.

When the plunger rod 60 is fully rotated towards the proximal end of injection device 1, the two legs of the U-bracket 81 are no longer supported by the longitudinal grooves of the plunger rod 60. Thus, the radial legs 86 at the proximal ends of the U-bracket can disengage the slits in the plunger driver 50. The spiral spring (not shown) coaxially arranged with the indicator rod 82 causes indicator assembly to move distally until the indicator 80 contacts the distal front surface of the distal housing part 3. This causes the distal protrusion of the indicator 80 to project through the indicator opening 83 provided in the centre of the distal wall of the distal housing part 3. This provides a visible and tactile indication to the user that the complete dose has been expelled.

Figure 7:
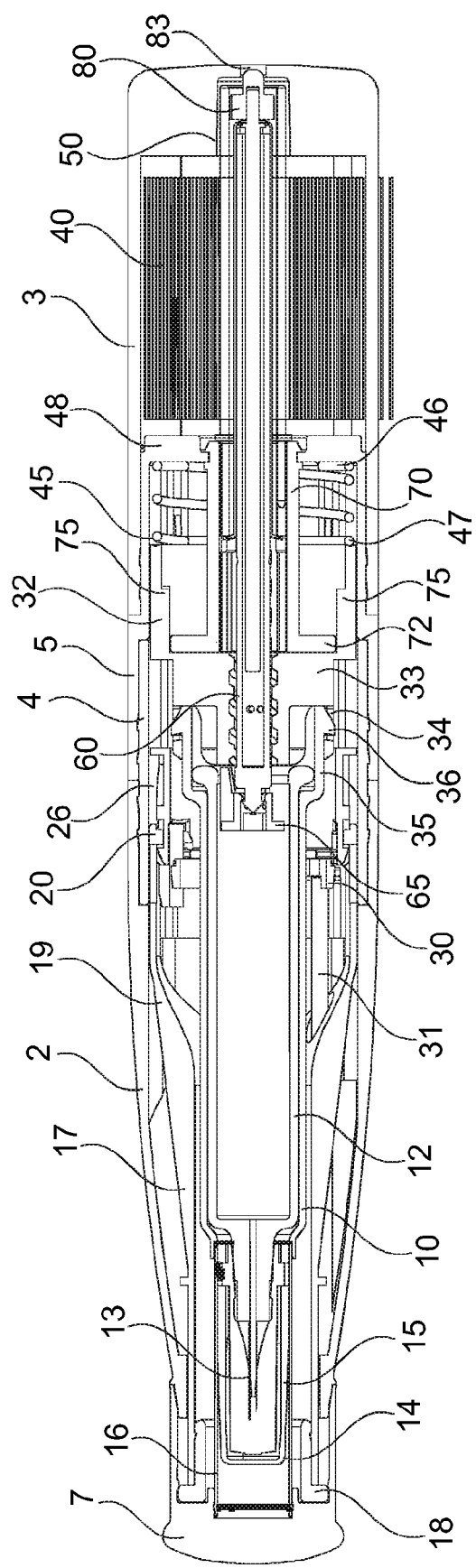
FIG. 7 shows a sectional view of the injection device according to the preferred embodiment of the invention in the initial position.

FIG. 7 shows a sectional view of the injection device 1 according to the preferred embodiment of the present invention in the initial position. In particular, FIG. 7 shows how the second spring 45 is located in the interior of the distal intermediate housing part 5. The distal end 46 of the second spring 45 is in contact with the inner surface of the distal radial wall of the distal intermediate housing part 5. Alternatively, it may be in contact with a ledge provided at the inside of the distal intermediate housing part, proximal to the distal radial wall of the distal intermediate housing part 5. The proximal end 47 of the second spring 45, on the other hand, abuts against a distal surface of the container driver 32.

Figure 8:
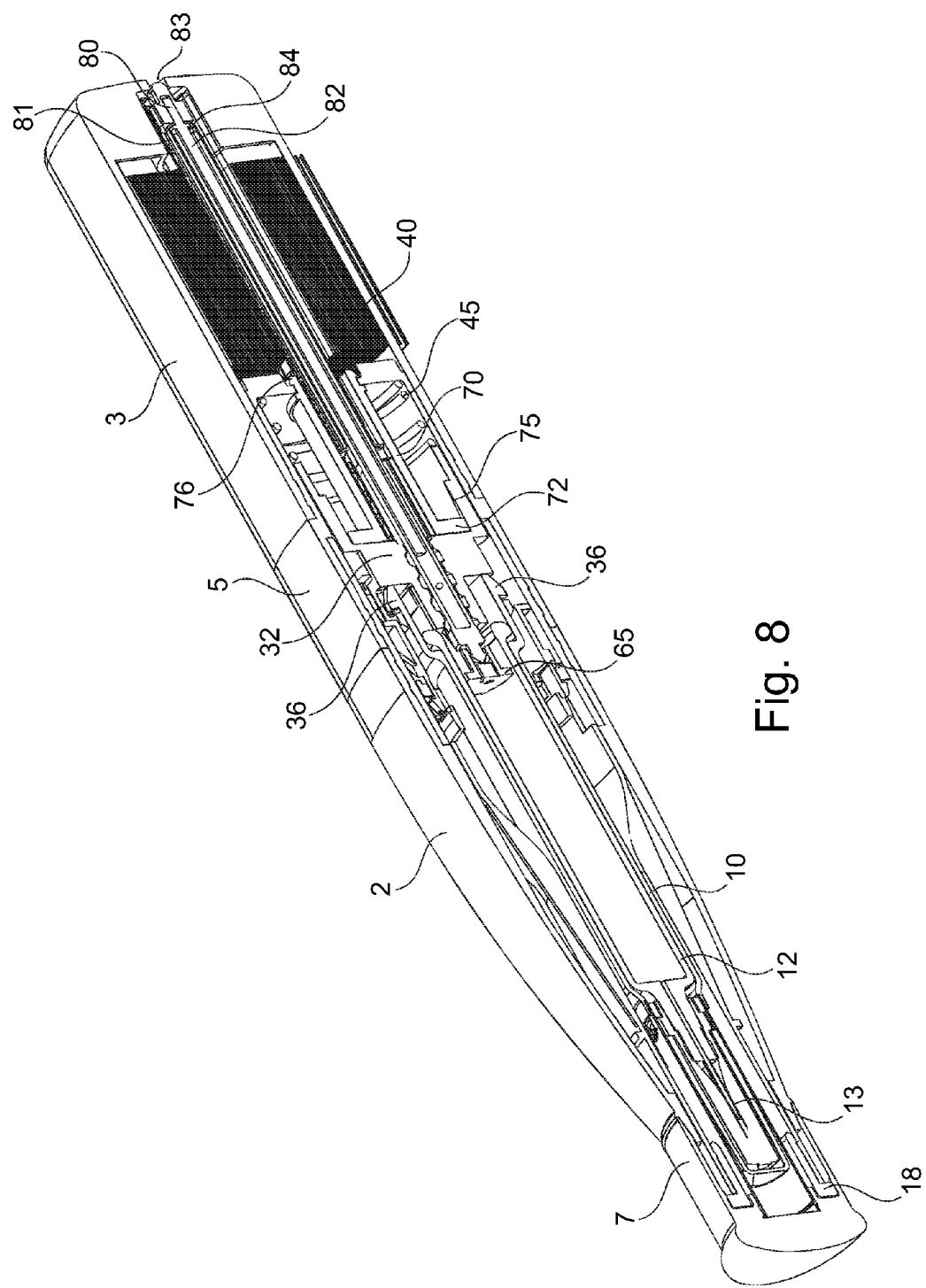
FIG. 8 shows a perspective view of the injection device according to the preferred embodiment of the invention in the initial position as shown in FIG. 7.

The same cross-sectional view is shown in FIG. 8, however as a perspective view in order to provide a different view of the various components relative to each other and their inter-engagement. Furthermore, in FIG. 8 the relative arrangement of the indicator 80, U-bracket 81, indicator rod 82, and injector distal opening 83 can be seen. The indicator rod 82 substantially extends within a central bore of the plunger rod 60. At the distal end of the injection device 1, a distal part of the injector rod 82 extends beyond the distal end of the plunger rod 60, and is received in an inner central bore of the indicator 80. The indicator rod 82 comprises a circumferential flange 84 adjacent to its distal end. Seen in axial direction, between the circumferential flange 84 and the proximal surface of the indicator 80, the intermediate part of the U-bracket 81 is located. As seen in FIG. 5, this intermediate part of U-bracket 81 comprises a throughhole through which the distal part of the indicator rod 82 extends. The two legs of the U-shaped bracket 81 extend in axial direction towards the proximal end of the plunger rod 60. At its proximal ends, the two legs of the U-bracket 81 each comprise a radial leg 86. This radial legs 86 project into corresponding radial openings in the plunger driver 50 (see FIG. 5).

Figure 9:
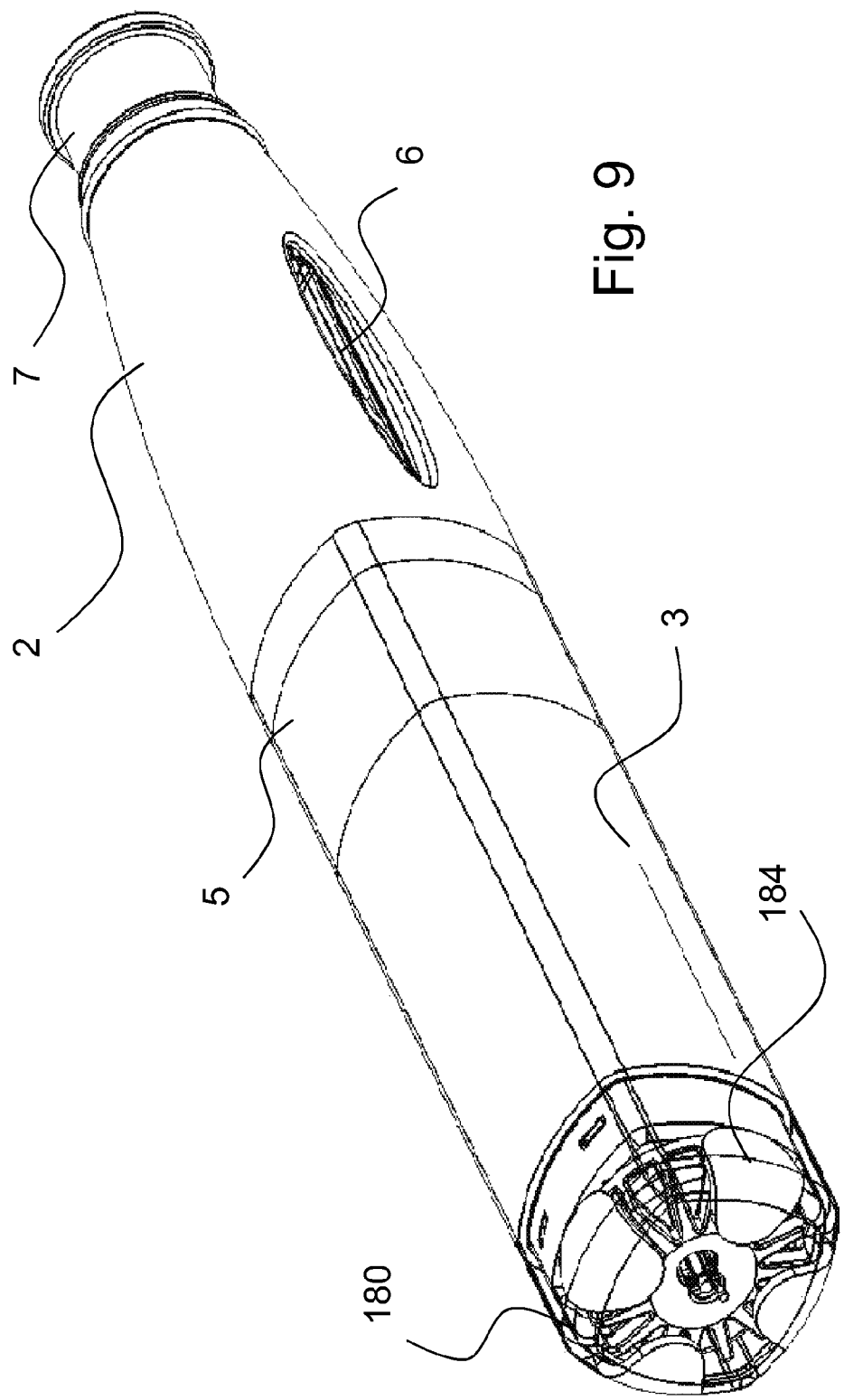
FIG. 9 shows a perspective view of a second preferred embodiment of the invention.

FIG. 9 shows a perspective view of a second preferred embodiment of the present invention. The injection device 100 shown in FIG. 9 is to a large extent identical to the injection device 1 according to the first preferred embodiment of the present invention. Same components are labelled with identical reference numerals. In the following, only the differences between the first and the second preferred embodiment will be explained in detail.

As shown in FIG. 9, the injection device 100 is different from the injection device 1 with respect to the indicator assembly that is provided to show end of dose. The structure for needle penetration and medicament injection shown in FIGS. 2 through 6 is also present in the injection device 100 of FIGS. 9 to 12.

Figure 10:
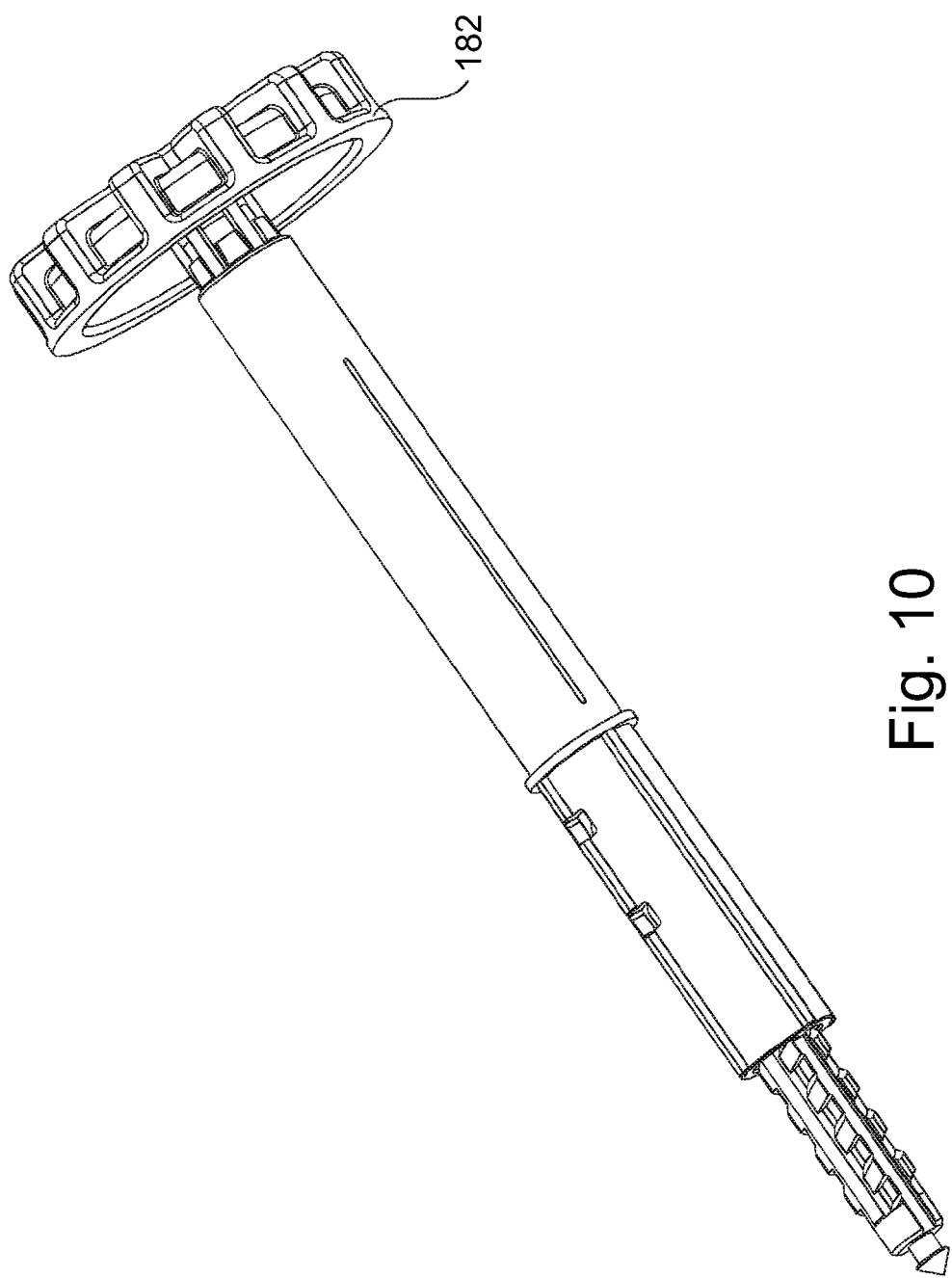
FIG. 10 shows a perspective view of details of the second preferred embodiment.

The second preferred embodiment shown in FIG. 9 comprises an indicator assembly 180 provided at the distal end of the housing. That is, the indicator assembly is preferably located distal to the plunger drive means 50, 70, and/or distal to the first energy accumulating member. The indicator assembly comprises a cap 180, in the embodiment shown transparent and having at least one opening 181 into which solid panels 184 are placed. In the embodiment shown in the drawings, four opposite openings 181 are provided. The four openings 181 are opposite with respect to the center axis of the injection device, i.e., they are located diametric. Through the transparent cap 180, the user can see a signalling element in the form of a rotatable element, such as a wheel or disk 182, which is also shown in FIG. 10.

Figure 11:
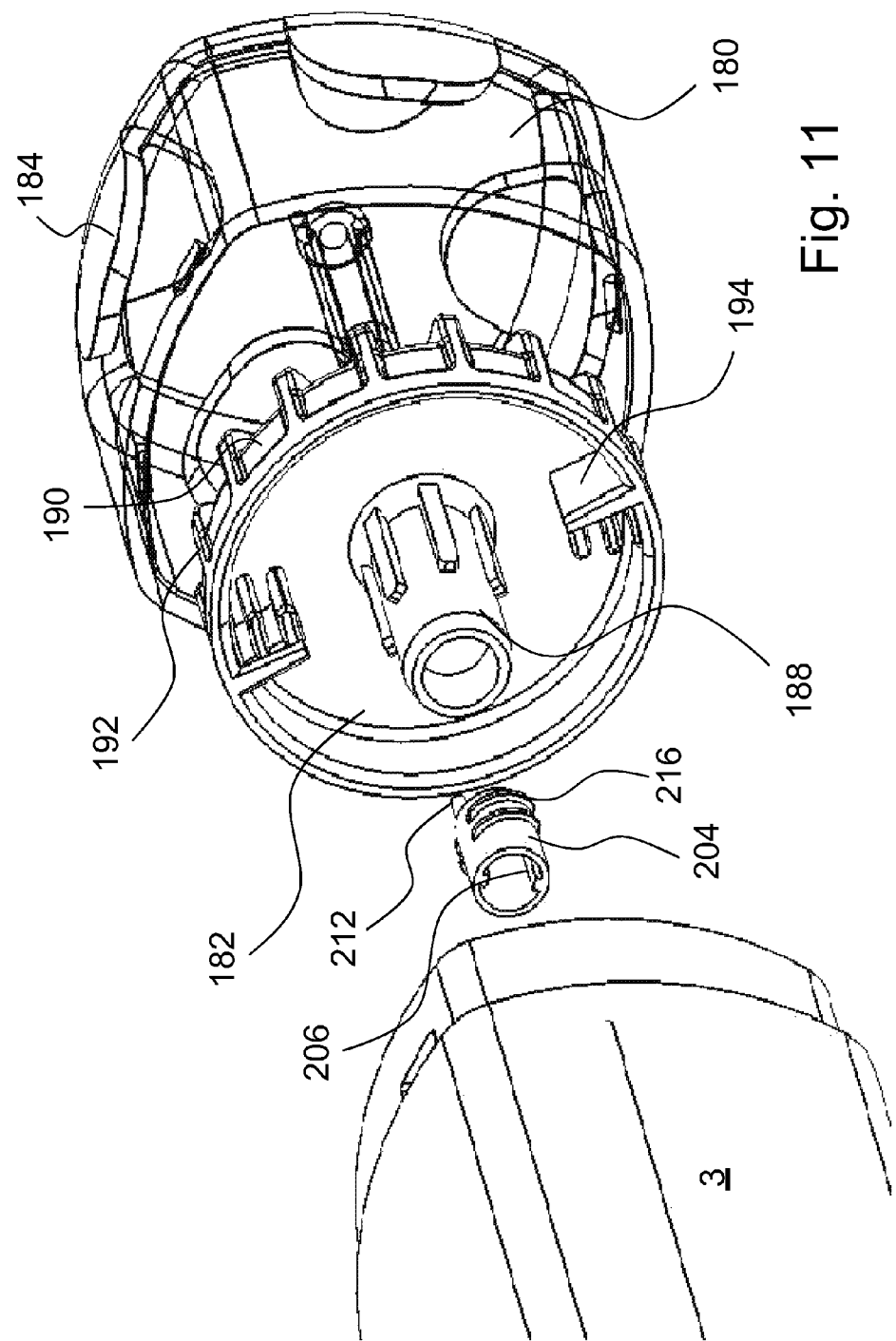
FIG. 11 shows a perspective view of details of the second preferred embodiment

As shown in FIG. 11, the rotatable disk 182 comprises a cylindrical proximal protrusion 188, such as a wheel hub. By means of this wheel hub 188, the rotatable disk 182 is connected to the distal end of the plunger driver 50. Thus, upon rotation of the plunger driver 50 by the first spring 40, also the rotatable disk 182 rotates. This can be seen by the user through the cap 180. Thus, the user can readily see that the device works properly and that an injection is in progress.

Figure 12:
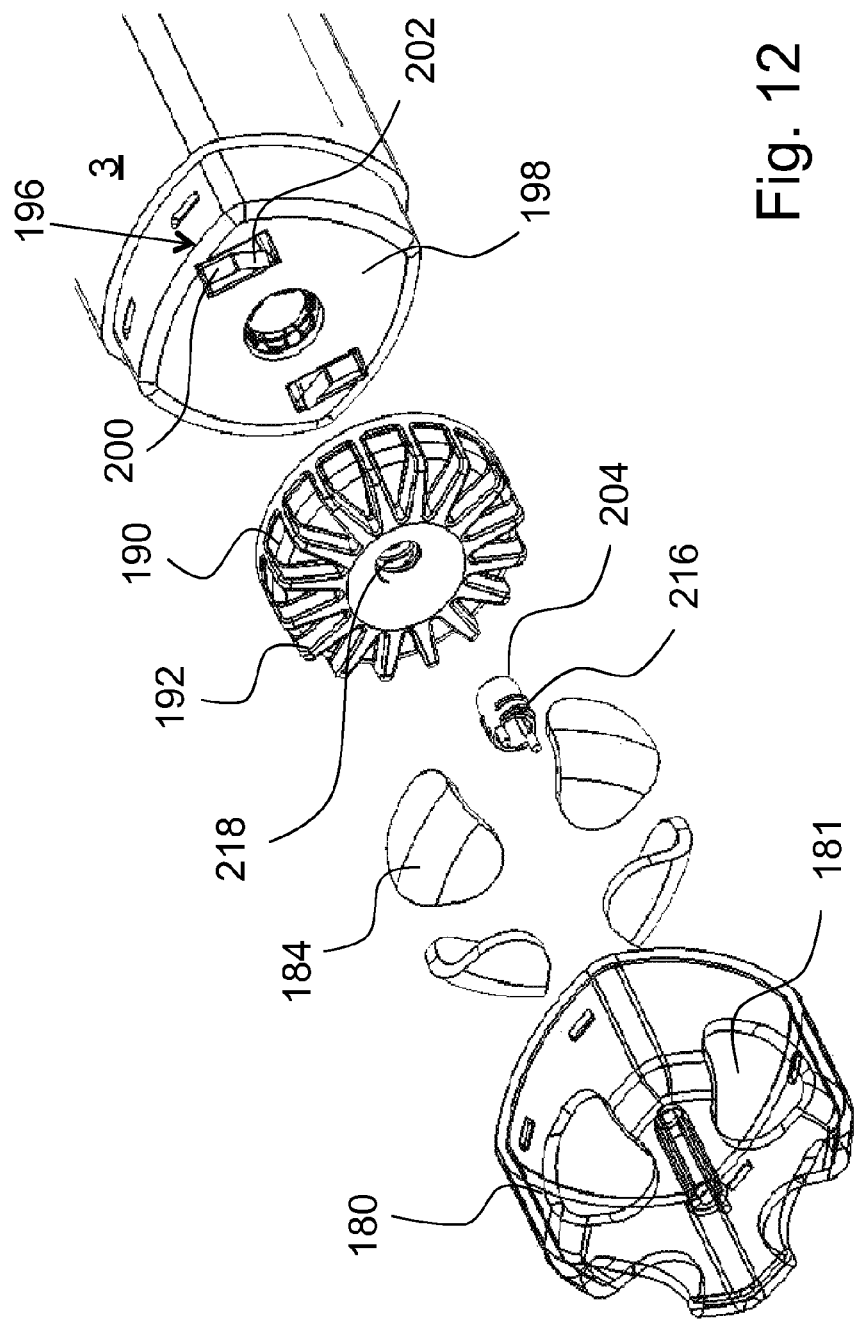
FIG. 12 shows a perspective view of details of the second preferred embodiment.

As also shown in FIG. 12, the rotatable disk 182 comprises a distal indication structure having a plurality of segments 190*a*, . . . , 190*i*, . . . , 190*n*. These segments 190 alternate with radial ribs 192, i.e. are separated from each other by radial ribs. The ribs 192 project from the surface of the rotatable disk in at least distal direction and extend radially with respect to the radial center of the injection device. When the rotatable disk 182 rotates, the alternating structure of ribs and segments are shown through the cap 180 as they pass the panels 184. In a preferred embodiment, the segments 190 and/or the ribs 192 constitute visual signalling members 190, 192. For example, the segment 190 or rib 192 shown through the cap 180 in the initial stage of the injection device 100 contains a first indication element, whereas the segment 190 or rib 192 shown through the cap in the final position of the injection probably comprises a second, different indication element so that the user can easily distinguish the initial stage prior to injection from the final stage after injection of the medicament. For example, the segments 190 are coloured in different colours. Alternatively (not shown in the drawings), the angular widths of the segments may vary, for example from a very small width to a wide width in order to distinguish the initial position from the final position.

Furthermore, these rotary injection indication mechanisms are arranged such that the progress of injection is shown through at least one opening provided at least in a distal end surface of the housing.

A further information mechanism available to the user is an audio signalling member. It comprises protrusions or ledges 194, FIG. 11, on a proximally directed surface of the rotatable disk 182. As seen in FIG. 11, the ledges are directed generally in the radial direction but may be arranged in other directions. These ledges 194 are intended to cooperate with flexible members 196 arranged on a distally directed end surface 198 of the distal housing part 3, FIG. 12. The flexible members 196 comprise at least one (two in the embodiment shown) arms 200 that extend generally in the same plane as the surface 198, with free ends having distally inclined surfaces 202, forming wedge-shaped distally directed protrusions.

Thus, when the rotatable disk 182 is rotating during injection as described above, the ledges 194 on the rotatable disk 182 will come in contact with the inclined surfaces of the protrusions 202 of the arms 200, thereby pressing the arms 200 in the proximal direction until the protrusions 202 are moved out of contact with the ledges 194. This will cause the arms 200 to flex back quickly, whereby the protrusions 202 of the arms 200 will hit the proximally directed surface of the rotatable disk 180, producing an audible sound. Thus during the rotation of the rotatable disk 182 the ledges 194 and arms 200 with their protrusions will cause sounds that are audible during the injection sequence until the rotatable disk stops at the end of the injection sequence.

Figure 13:
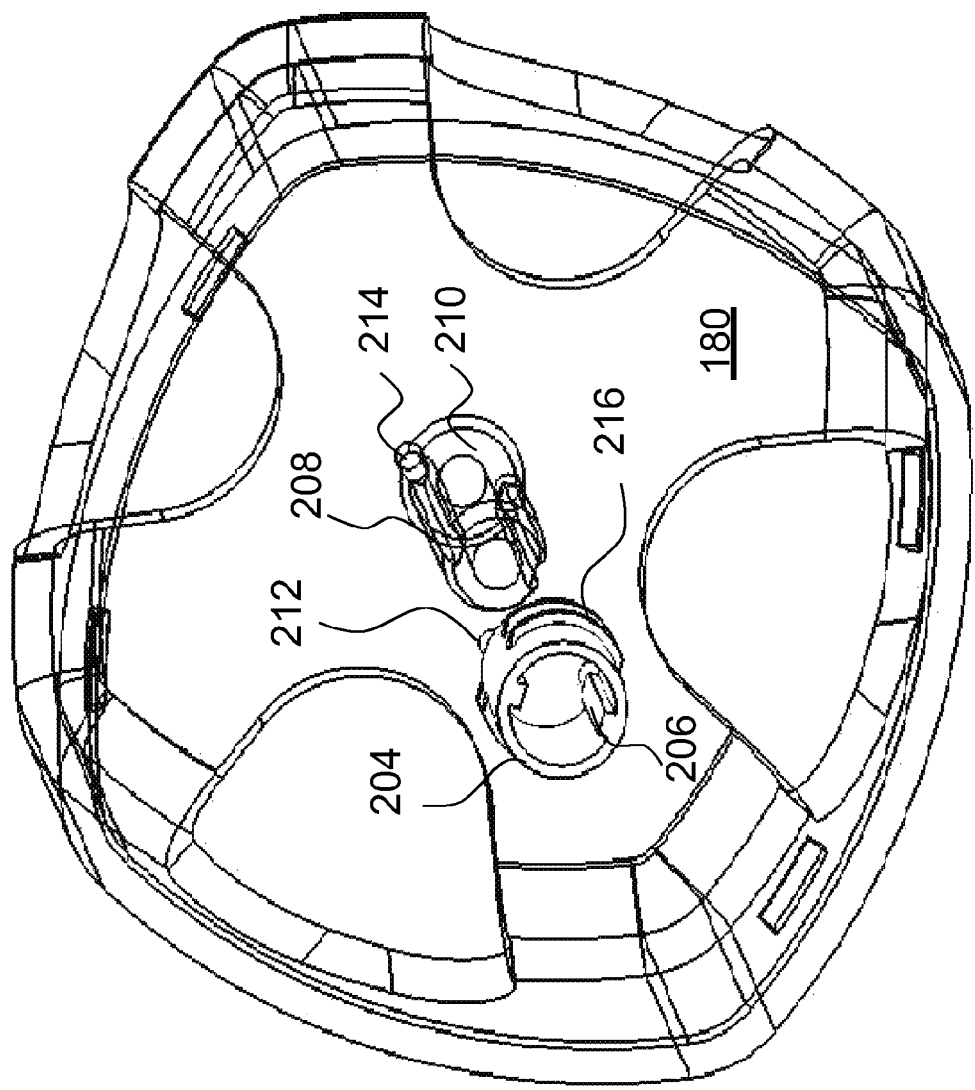
FIG. 13 shows a perspective view of details of the second preferred embodiment.

In order to further provide the user with information during the injection sequence, a tactile information member is arranged at the distal end of the device. It comprises a tactile signalling member 204, FIG. 11, having a generally tubular shape. On its inner surface it is arranged with longitudinally directed ledges 206 (two in the embodiment shown) positioned diametrically on opposite sides. These ledges 206 are arranged to be fitted into longitudinally extending grooves 208 in a centre tap or column 210 attached to the inner surface of the cap 180 and directed in the proximal direction, as seen in FIG. 13.

Further the driver 204 is arranged with at least one distally extending protrusion 212 attached to its distally directed end surface. In the embodiment shown, there are two protrusions 212 on the driver 204. Further, the cap 180 is arranged with corresponding number of passages 214, FIG. 13, through its end surface, positioned on the side of the column 210 of the cap 180. The protrusions 212 of the driver 204 has such lengths that they will protrude through the passages 214 the cap 180 and a distance above the distally directed end surface of the cap 180 when the driver 204 is in its most distal position along the column 210 of the cap 180. The column 210 of the cap 180 has a diameter somewhat less than the inner diameter of the driver 204, whereby the driver is rotationally locked to the tap but may slide along the tap as will be explained.

The outer surface of the driver is arranged with thread segments 216, e.g. like spirally extending ledges. These cooperate with corresponding threads or spirally extending grooves 218, FIG. 12, on a central passage of the proximal protrusion 188 of the rotatable disk 182.

Figure 14A:
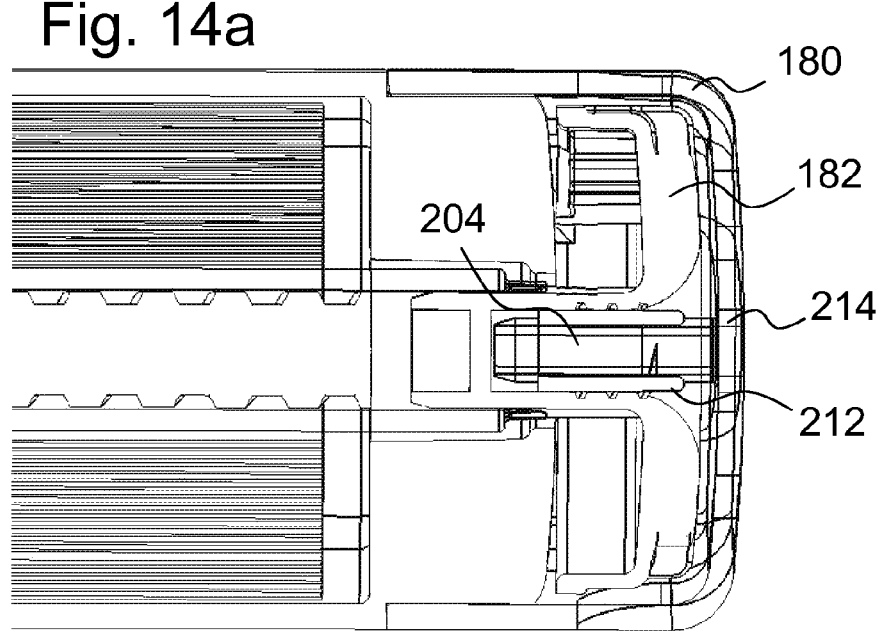
FIGS. 14a, 14b show detailed cross-sectional views of the tactile indication mechanism of the second preferred embodiment.
Figure 14B:
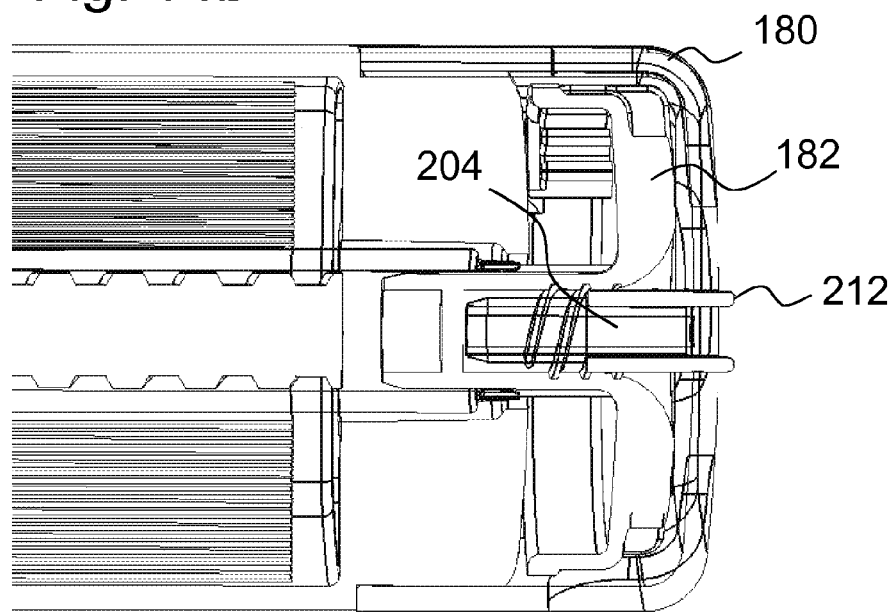

During the injection sequence, the rotatable disk is rotating continuously, as described above. On the other hand, the tactile signalling member is locked rotationally due to the longitudinal ledges 206 fitting into the grooves 208 of the cap 180, which in turn is fixed in relation to the distal housing part 3. The rotation of the rotatable disk 182 will thus cause its thread segments 218 to act on the thread segments 216 of the tactile signalling member 204, whereby the tactile signalling member 204 will be diplaced linearly in the distal direction from an initial position, FIG. 14a. The linear movement will in turn cause the distally directed protrusions 212 of the tactile signalling member to extend through the passages 214 and protrude above the surface of the cap 180, FIG. 14b. Thus, when a patient or user during the injection sequence is holding a finger against the distally directed end surface of the cap 180, he/she will feel the protrusions 212 rising up from the surface.

Thereby a positive tactile feeling and thus information about the progress of the injection is obtained. In this context it is to be understood that the length of the protrusions as well as initial position of the driver in relation to the rotatable disk and the pitch of the thread segments may be altered in many ways in order to obtain the desired, predetermined end result. For example, the protrusions may be positioned just below the distal surface of the cap at the start of the injection sequence, whereby the protrusions will provide tactile information right from the start of the injection sequence. On the other hand, the configuration may be such that the protrusions extend through the distal surface of the cap only at the very end of the injection sequence, when the tactile signalling member has reached an end position, thereby providing tactile information that indicate end of injection sequence, i.e. that the device is safe to remove. Also, the pitch of thread of segments 216, 218 may be adapted to obtain a predetermined speed of displacement of the tactile signalling member during injection. It is also to be understood that the tactile information as well as the audible information and visual information may be used and provided simultaneously to the user when handling the device.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

It is to be understood that the embodiment described above and shown in the drawings is to be regarded only as a non-limiting example of the invention and that it may be modified in many ways within the scope of the patent claims.

The invention claimed is:

1. An injection device, comprising:
   a housing;
   a container holder within the housing configured for accommodating a medicament container, the medicament container having a needle attached to one end thereof and a stopper sealingly and slidably arranged inside the medicament container at the other end thereof;
   a drive unit, comprising a plunger rod; a plunger driver slidably arranged in relation to the plunger rod, rotationally locked to the plunger rod, and rotatable in relation to the housing; and a first energy accumulating member arranged in an interior of the housing, configured to accumulate and store energy, and operationally associated with the plunger driver; wherein the plunger driver is releasable such that due to an output torque from the first energy accumulating member, the plunger driver is enabled to be rotated and the plunger rod is urged toward a proximal end of the injection device, whereby an injection is performed; and
   an injection indication mechanism configured for indicating progress of the injection and comprising a tactile signaling member and a drive mechanism for driving the tactile signaling member, the drive mechanism being coupled to the plunger driver at a distal end of the plunger driver, and the injection indication mechanism being such that progress of the injection is felt by a user;
   wherein the tactile signaling member comprises at least one distally directed protrusion arranged to extend through at least one passage arranged in an end surface of the housing, and the drive mechanism is a rotary drive mechanism rotationally locked to the plunger driver such that rotation of the rotary drive mechanism during the injection drives the tactile signaling member in a distal direction, thereby indicating progress of the injection.

2. The injection device of claim 1, wherein the tactile signaling member includes thread segments configured to cooperate with corresponding thread segments on the rotary drive mechanism.

3. The injection device of claim 2, wherein:
a pitch of the thread segments is such that displacement of the tactile signaling member has a predetermined speed; or
a length of the at least one protrusion provides a predetermined timing and tactile experience of progress of the injection; or
at least one of an initial position and an end position of the tactile signaling member in relation to a distal end surface of the injection device provides predetermined characteristics of progress of the injection.

4. The injection device of claim 1, wherein the rotary drive mechanism further comprises an audio signaling member configured to indicate progress of the injection audibly to the user.

5. The injection device of claim 4, wherein the audio signaling member comprises at least one flexible member and at least one impact member, and during rotation of the rotary drive mechanism, the impact member acts on the flexible member, thereby producing a sound.

6. The injection device of claim 5, wherein the flexible member comprises at least one arm that is generally flush with a distally directed surface of a distal portion of the housing, the arm comprises a free end having a distally inclined surface forming a wedge-shaped distally directed protrusion, and the at least one impact member comprises at least one protrusion on the rotary drive mechanism arranged to move in and out of contact with the distally directed protrusion during rotation.

7. The injection device of claim 1, wherein the rotary drive mechanism further comprises a visual signaling member configured to indicate progress of the injection visually to the user through at least one opening provided at least in a distal end surface of the housing.

8. The injection device of claim 7, wherein the visual signaling member comprises at least one indication element for informing the user that the injection device is ready for an injection, that the injection is in progress, and that the injection has ended.

9. The injection device of claim 8, wherein the visual signaling member includes a rotatable disk.

10. An injection device, comprising:
a housing;
a container holder within the housing configured for accommodating a medicament container, the medicament container having a needle attached to one end thereof and a stopper sealingly and slidably arranged inside the medicament container at the other end thereof;
a drive unit, comprising a plunger rod; a plunger driver slidably arranged in relation to the plunger rod, rotationally locked to the plunger rod, and rotatable in relation to the housing; and a first energy accumulating member arranged in an interior of the housing, configured to accumulate and store energy, and operationally associated with the plunger driver; wherein the plunger driver is releasable such that due to an output torque from the first energy accumulating member, the plunger driver is enabled to be rotated and the plunger rod is urged toward a proximal end of the injection device, whereby an injection is performed; and
an injection indication mechanism configured for indicating progress of the injection and comprising a tactile signaling member and a drive mechanism for driving the tactile signaling member, the drive mechanism being coupled to the plunger driver at a distal end of the plunger driver, and the injection indication mechanism being such that progress of the injection is felt by a user;
wherein the drive mechanism is a rotary drive mechanism rotationally locked to the plunger driver such that rotation of the rotary drive mechanism during the injection drives the tactile signaling member in a distal direction, thereby indicating progress of the injection.

11. The injection device of claim 10, wherein the tactile signaling member includes thread segments configured to cooperate with corresponding thread segments on the rotary drive mechanism.

12. The injection device of claim 11, wherein:
a pitch of the thread segments is such that displacement of the tactile signaling member has a predetermined speed; or
at least one of an initial position and an end position of the tactile signaling member in relation to a distal end surface of the injection device provides predetermined characteristics of progress of the injection.

13. The injection device of claim 10, wherein the rotary drive mechanism further comprises an audio signaling member configured to indicate progress of the injection audibly to the user.

14. The injection device of claim 13, wherein the audio signaling member comprises at least one flexible member and at least one impact member, and during rotation of the rotary drive mechanism, the impact member acts on the flexible member, thereby producing a sound.

15. The injection device of claim 14, wherein the flexible member comprises at least one arm that is generally flush with a distally directed surface of a distal portion of the housing, the arm comprises a free end having a distally inclined surface forming a wedge-shaped distally directed protrusion, and the at least one impact member comprises at least one protrusion on the rotary drive mechanism arranged to move in and out of contact with the distally directed protrusion during rotation.

16. The injection device of claim 10, wherein the rotary drive mechanism further comprises a visual signaling member configured to indicate progress of the injection visually to the user through at least one opening provided at least in a distal end surface of the housing.

17. The injection device of claim 16, wherein the visual signaling member comprises at least one indication element for informing the user that the injection device is ready for an injection, that the injection is in progress, and that the injection has ended.

18. The injection device of claim 17, wherein the visual signaling member includes a rotatable disk.

* * * * *